United States Patent
Sun

(10) Patent No.: US 9,937,105 B2
(45) Date of Patent: *Apr. 10, 2018

(54) HIGH STRENGTH DENTAL MATERIAL

(71) Applicant: DENTSPLY International Inc., York, PA (US)

(72) Inventor: Benjamin J Sun, York, PA (US)

(73) Assignee: DENTSPLY SIRONA INC., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/665,317

(22) Filed: Mar. 23, 2015

(65) Prior Publication Data

US 2015/0196462 A1    Jul. 16, 2015

Related U.S. Application Data

(63) Continuation of application No. 13/301,181, filed on Nov. 21, 2011, now Pat. No. 9,011,150.

(60) Provisional application No. 61/416,382, filed on Nov. 23, 2010.

(51) Int. Cl.
*A61K 6/093*    (2006.01)
*A61C 13/00*    (2006.01)
*A61K 6/083*    (2006.01)
*A61K 6/00*    (2006.01)
*A61K 6/02*    (2006.01)

(52) U.S. Cl.
CPC ............ *A61K 6/083* (2013.01); *A61K 6/0088* (2013.01); *A61K 6/0091* (2013.01); *A61K 6/02* (2013.01)

(58) Field of Classification Search
CPC .......... A61K 6/083; C08L 33/08; C08L 33/10
USPC .......................................... 523/115; 526/301
See application file for complete search history.

(56) References Cited

U.S. PATENT DOCUMENTS 9,011,150 B2 *    4/2015    Sun ..................... A61K 6/083
                                                     433/215

FOREIGN PATENT DOCUMENTS

EP    0733668    *    9/1996
JP    2000-007753    *    1/2000

* cited by examiner

*Primary Examiner* — Tae H Yoon
(74) *Attorney, Agent, or Firm* — David A. Zdurne; Douglas J. Hura; Leana Levin

(57) ABSTRACT

The invention provides a high strength dental composition including polymerizable dental resins. The dental composition is useful as restorative material and for making various dental devices, such as artificial teeth, crowns and bridges of high strength dental polymeric material.

17 Claims, No Drawings

HIGH STRENGTH DENTAL MATERIAL

RELATED APPLICATIONS

This is a continuation application of U.S. patent application Ser. No. 13/301,181, filed on Nov. 21, 2011 and now issued as U.S. Pat. No. 9,011,150, which claims the benefit of and priority to U.S. Provisional Patent Application Ser. No. 61/416,382, filed on Nov. 23, 2010, which is herein incorporated by reference for all purposes.

FIELD OF INVENTION

The present invention relates generally to high strength materials for making long-term dental crowns, bridges, inlays, onlays, veneers, implants, and other dental restorations. High strength polymerizable resins and related composites are used to make the dental restorations, especially dental crown, bridge and veneer.

BACKGROUND OF THE INVENTION

Dental restorations, such as veneers, crowns and bridges, are used to restore or replace lost tooth structure, teeth, or oral tissue.

SUMMARY OF THE INVENTION

In one aspect, the present invention is directed to a high strength dental composition comprising: about 1 to about 99% wt of one or more urethane di or multi(meth)acrylate derivatives of 1,3-bis(isocyanatomethyl)cyclohexane characterized by one of the following formulas:

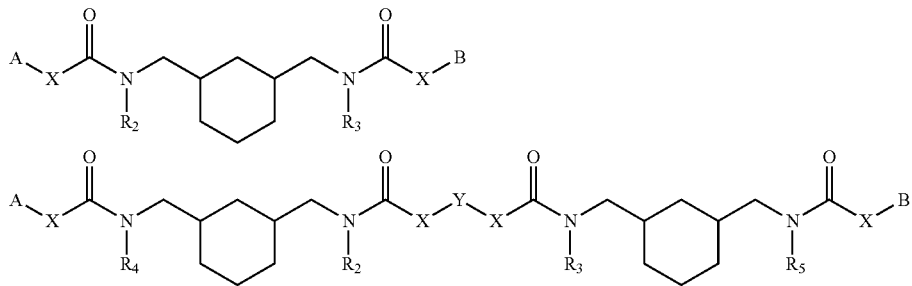

in which: X is oxygen, nitrogen, or $NR_1$, where: $R_1$ is hydrogen, a C1-C14 alkyl group, a C6-C14 cyclic group, C1-C14 cyclic alkyl group, a C6-C14 aromatic group, a C1-C14 aromatic alkyl group, or any combination thereof; $R_2$, $R_3$, $R_4$ and $R_5$ is hydrogen, a C1-C14 alkyl group, a C6-C14 cyclic group, C1-C14 cyclic alkyl group, a C6-C14 aromatic group, a C1-C14 aromatic alkyl group, or any combination thereof; Y is a C1-C14 alkyl group, a C6-C14 cyclic group, a C1-C14 cyclic alkyl group, a C6-C14 aromatic group, a C1-C14 aromatic alkyl group, or any combination thereof; A and B independently of each other stand for one of the following formulas:

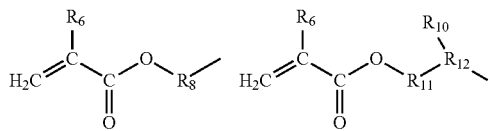

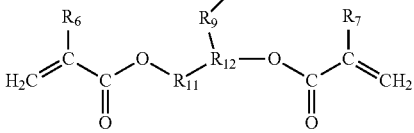

where: $R_6$ and $R_7$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms; $R_8$ and $R_9$ is a C1-C12 difunctional alkylene, a C1-C12 alkyl group, a C6-C12 cyclic group, a C1-C12 cyclic alkyl group, a C6-C12 aromatic group, a C1-C12 aromatic alkyl group, or any combination thereof, which can be interrupted by oxygen, sulfur, or otherwise atoms; $R_{10}$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms; $R_{11}$ represents a C1-C14 difunctional alkylene, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms; and $R_{12}$ represents a C1-C8 trifunctional alkyl group, which can be interrupted by oxygen, sulfur, or otherwise atoms; and about 0.001 to about 10% wt of an initiator for the radical polymerization.

In another aspect of the present invention, it is contemplated that the high strength dental composition has one or any combination of the following features the composition further comprises about 5% to about 95% of at least one filler; the composition includes about 10% to 50% wt of one or more of the urethane di or multi(meth)acrylate derivatives; the composition includes about 15% to 40% wt of one or more of the urethane di(meth)acrylate derivatives; about 30% to about 90% wt fillers; and 0.005% to about 5% of an initiator for the radical polymerization; A and B are the same; the composition includes a flexural modulus of at least about 400,000 psi and a flexural strength of at least about 20,000 psi, the composition includes a flexural modulus of at least about 800,000 psi and a flexural strength of at least about 22,000 psi; the composition is substantially free of a filler; the composition includes a flexural modulus of at least about 450,000 psi and a flexural strength of at least about 24,000 psi; a flexural modulus of at least about 1,000,000 psi and a flexural strength of at least about 26,000 psi, or any combination thereof

DETAILED DESCRIPTION OF THE INVENTION

In general, the present invention is directed to an improved high strength polymerizable composition, processes of forming the composition, as well as articles formed by the high strength polymerizable composition, by the processes, or both. Advantageously, the polymerizable composition can be employed to form dental components with desirable high strength characteristics. This high strength material enables the preparation of highly demanded and durable restorations, such as esthetic metal-free long term veneers, crowns and bridges to replace alloy or ceramic based veneers, crowns and bridges. These polymerizable dental materials (e.g., composites) may be useful in tooth restorative fillings, adhesives, cements, denture base materials, orthodontic materials and sealants, for repair of defects in natural dentition, and to form crowns, bridges, full dentures, partial dentures, custom trays, artificial teeth, repairs for natural teeth, veneers, denture repairs, retainers, orthodontic components, provisional dental devices, inlays, onlays, orthodontic appliances, oral orthopedic appliances, maxillofacial prostheses, obturators, occular prostheses and other dental restorations. Dental materials containing polymerizable resins and filler particles often are used to prepare the dental restorations. Such dental materials can be self (chemically)-curable, heat-curable, light-curable, or dual-curable. The dental materials are cured and hardened by different chemical mechanisms to form strong and durable materials for various dental applications. The polymerizable composition typically includes at least one urethane and/or urea resin (e.g., urethane di-(meth)acrylate or multi(meth)acrylate derivatives of isocyanatomethyl cyclohexane), and optionally one or more additives that can include, without limitation, at least one filler (e.g., glass particles), an initiator, a catalyst, an accelerator, an inhibitor, surfactant, or combinations thereof or others.

Polymerizable Materials
Polymerizable Acrylic Compounds

Turning now in greater detail to the individual components of the overall composition. The material herein will typically include a first polymerizable component that includes at least one polymerizable acrylic compound. The polymerizable acrylic compound (e.g., first polymerizable component) will typically be present in an amount of at least 1% wt and less than 99% wt the overall polymerizable composition. More particularly, the polymerizable acrylic compound (e.g., first polymerizable component) will typically be present in an amount of at least 10% wt, and more preferably at least about 15% wt the overall polymerizable composition. The overall polymerizable composition also typically includes less than about 50% wt and more typically less than about 40% wt of the polymerizable acrylic compound. For example, the polymerizable acrylic compound will typically be present in a range of about 10% to about 50%, and more typically from about 15% to about 40% wt of the overall polymerizable composition.

Examples of polymerizable acrylic compounds that may be used in the composition of this invention, include, but are not limited to, mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol di(meth)acrylate, tetraethylene glycol di(meth)acrylate, 1,3-propanediol diacrylate, 1,3-propanediol dimethacrylate, 1,4-butanediol di(meth)acrylate, trimethylolpropane tri(meth)acrylate, 1,2,4-butanetriol trimethacrylate, 1,4-cyclohexanediol diacrylate, 1,4-cyclohexanediol dimethacrylate, cyclohexane dimethanol diacrylate, cyclohexane dimethanol dimethacrylate, 1,6-hexanediol di(meth)acrylate, pentaerythritol triacrylate, pentaerythritol tetraacrylate, pentaerythritol tetramethacrylate, sorbitol hexacrylate, 2,2-bis[4-(2-hydroxy-3-acryloyloxypropoxy)phenyl]propane; Tris(2-hydroxy ethyl) isocyanurate triacrylate, 2,2-bis[4-(2-hydroxy-3-methacryloyloxypropoxy)phenyl]propane (Bis-GMA); modified Bis-GMA (the reaction product of Bis-GMA and 1,6 diisocyanatohexane); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), polyurethane dimethacrylate (PUDMA); 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); alkoxylated pentaerythritol tetraacrylate; polycarbonate dimethacrylate (PCDMA); the bis-acrylates and bis-methacrylates of polyethylene glycols; and copolymerizable mixtures of acrylated monomers and acrylated oligomers.

Preferably, the polymerizable acrylic compound is urethane dimethacrylate derivative of (isocyanatomethyl)cyclohexane (e.g., 1,3-bis(isocyanatomethyl)cyclohexane) that may be selected from compounds characterized by one of the following formulas:

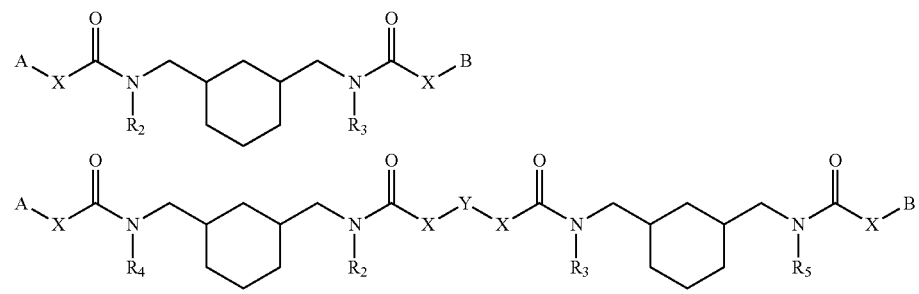

in which:

X is oxygen, nitrogen, or NR1, where R1 is hydrogen, a C1-C14 alkyl group, a C6-C14 cyclic group, C1-C14 cyclic alkyl group, a C6-C14 aromatic group, a C1-C14 aromatic alkyl group, or any combination thereof;

R2, R3, R4 and R5 is hydrogen, a C1-C14 alkyl group, a C6-C14 cyclic group, C1-C14 cyclic alkyl group, a C6-C14 aromatic group, a C1-C14 aromatic alkyl group, or any combination thereof;

Y is a C1-C14 alkyl group, a C6-C14 cyclic group, a C1-C14 cyclic alkyl group, a C6-C14 aromatic group, a C1-C14 aromatic alkyl group, or any combination thereof. Examples of Y include as 1,3-cyclohexanedimethylene, 1,4-cyclohexanedimethylene, or otherwise;

A and B independently of each other stand for:

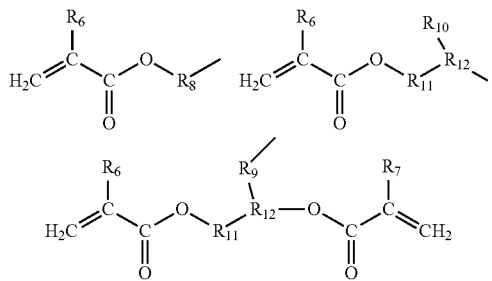

where:

R6 and R7 is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms;

R8 and R9 is a C1-C12 difunctional alkylene, a C1-C12 alkyl group, a C6-C12 cyclic group, a C1-C12 cyclic alkyl group, a C6-C12 aromatic group, a C1-C12 aromatic alkyl group, or any combination thereof, which can be interrupted by oxygen, sulfur, or otherwise atoms;

R10 is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms;

R11 represents a C1-C14 difunctional alkylene, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms; and R12 represents a C1-C8 trifunctional alkyl group, which can be interrupted by oxygen, sulfur, or otherwise atoms.

It is contemplated that A, B, X, Y, R1, R2, R3, R4, R5, R6, R7, R8, R9, R10, R11, R12, or any combination thereof may be further inserted, substituted or non-substituted. When inserted or substituted, possible substituents may include, but are not limited to, one or more of the groups halogen, O, S, NH, CO—NH, NH—CO, NH—COO, O—CO—NH, NH—CO—NH, —OCH3, —OH, —CN, —NO2, —COOH, —COOCH3, or any combination thereof, though not required.

Furthermore, urethane di(meth)acrylate derivates in which A and B have the same meaning are preferred.

Particularly preferred non-limiting urethane di(meth) acrylate derivates may include:

UCDPHMA

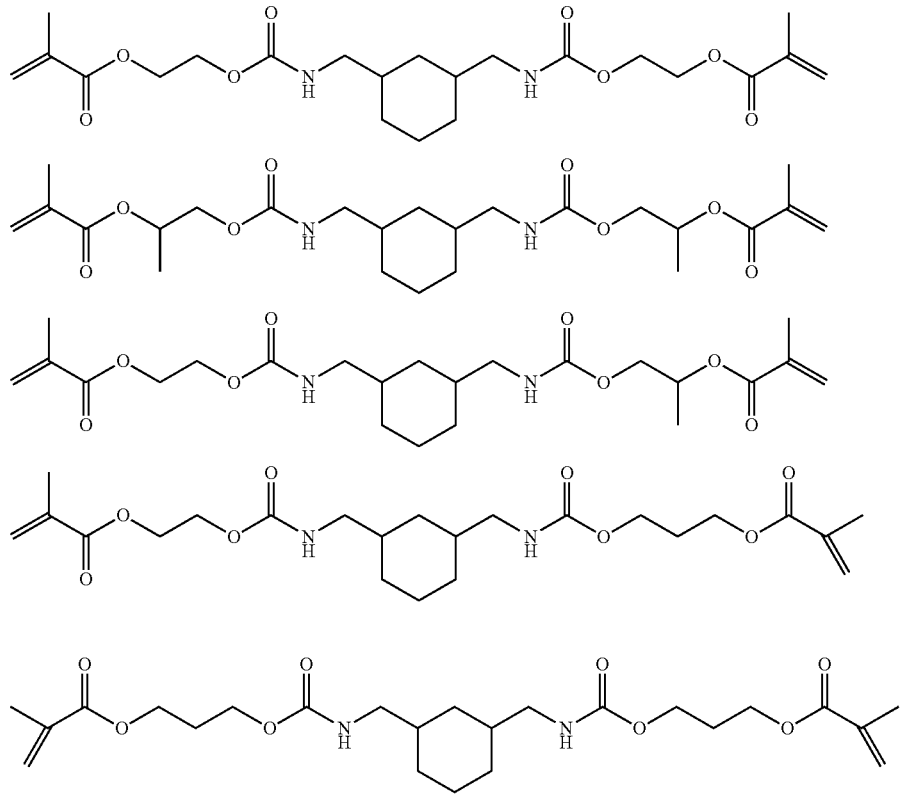

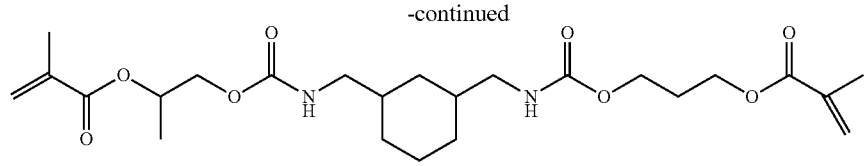

Particularly more preferred urethane di(meth)acrylate derivates may include:
UCDPMAA

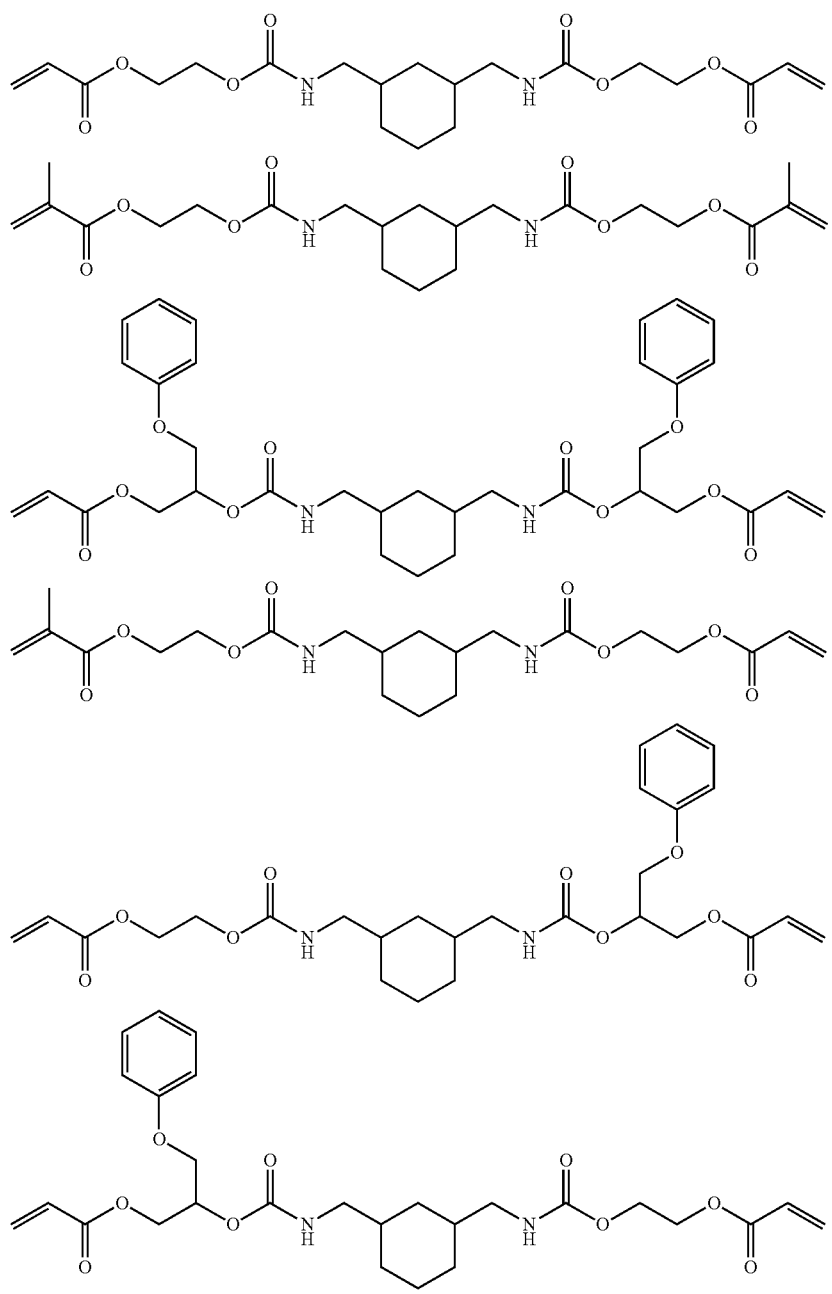

The urethane di(meth)acrylate derivates according to the invention can be prepared as disclosed below in Example 1 and/or Example 2.

In one preferred embodiment, the material may further include a second polymerizable component. The second polymerizable component may include about 0% to about 80%, and more preferably about 2% to 30% wt (e.g., 3% to about 10%) of one or more additional crosslinker monomers. Additional crosslinker monomers may include any combination of the polymerizable acrylic compounds discussed herein. Preferred additional crosslinker monomers include, but are not limited to Tris(2-hydroxyethyl)isocyanurate triacrylate (Sartomer SR 368), 2-propenoic acid, 2-methyl-1,2-ethanediyl-bis(oxy-2,1-ethanediyl)ester (TEGDMA), or otherwise, and combinations thereof.

Polymerization System

The material herein may include at least one initiating component (e.g., system) to effectuate curing of the material. The initiating component will typically be present in an amount of at least 0.001% wt, and more preferably at least about 0.005% wt the overall polymerizable composition. The overall polymerizable composition also typically includes less than about 10% wt and more typically less than about 5% wt of the initiating component. For example, the initiating component will typically be present in a range of about 0.001% to about 10%, and more typically from about 0.005% to about 5% wt of the overall polymerizable composition.

Polymerization may be initiated by irradiating the polymerizable dental materials with visible light or blue light preferably having a wavelength in the range of about 380 to about 500 nm. A standard dental blue light-curing unit or a lab visible light curing (VLC) unit, such as Triad® 2000 light curing unit or Enterra™ VLC curing unit (both are sold by Dentsply International, York, Pa.), can be used to irradiate the dental materials. A preferred initiating component may be a photoinitiator, which causes polymerization to be initiated upon exposure to activating wavelengths of light and/or a reducing compound. In one embodiment, the photoinitiator may be a diketone based for example camphorquinone (CQ). In another embodiment the photoinitiator may be selected from the class of acylphosphine oxides. Examples of acylphosphine oxides may include, but not limited to, monoacyl phosphine oxide derivatives, bisacyl phosphine oxide derivatives, and triacyl phosphine oxide derivatives. A preferred acylphosphine oxides may be, 2,4,6-trimethylbenzoyl-diphenyl-phosphine oxide (Lucirin-TPO) that may be used as the initiating component. In one preferred embodiment, an initiating system may be present (e.g., "ALF") comprising camphorquinone (CQ); butylated hydroxytoluene (BHT); N, N-dimethylaminoneopentyl acrylate, γ-methacryloxypropyl-trimethoxysilane and methacrylic acid. The "ALF" initiating system may be present in an amount ranging from about 0.05% wt to about 0.45% wt, and preferably from about 0.15% wt to about 0.35% wt of the overall polymerizable composition. It is appreciated that in one embodiment, the material may include an initiating system comprising both the "ALF" initiating system and Lucirin-TPO for curing the composition.

Other initiating components may include, but are not limited to room temperature or heat activating catalyst components (e.g., system) for curing polymerizable materials (e.g., dental materials) of the invention. For example a peroxide capable of producing free radicals when activated by a reducing agent at room temperature or by heating. Preferred peroxides may include benzyl peroxide, lauryl peroxide or otherwise and combinations thereof. Heat-activated polymerization initiating compounds may be included to provide a heat-curable polymerizable material. The peroxides generate free radicals to initiate polymerization and hardening of the composition at elevated temperature. Peroxides such as dibenzoyl peroxide (BPO), di-p-chlorobenzoyl peroxide, di-2,4-dichlorobenzoyl peroxide, tertiary butyl peroxybenzoate, methyl ethyl ketone peroxide, ditertiary butyl peroxide, dicumyl peroxide and cumene hydroperoxide, and the like can be used.

A room temperature initiating component (e.g., activating system) may be included to provide a self-curing polymerizable material. It is appreciated that the self curing polymerizable material may be prepared from at least two paste components. For example, one component may be provided as a base paste and the other component as a catalyst paste. In one embodiment, the base paste typically contains at least one polymerizable monomer, a free-radical polymerization accelerator such as a tertiary amine, and fillers. Meanwhile, the catalyst paste typically includes at least one polymerizable monomer (either the same or different from the base component, a free-radical polymerization initiator such as dibenzoyl peroxide, and fillers. To prepare the composition, the amine-containing base and peroxide-containing catalyst pastes are combined and mixed together. As the pastes are mixed together, the catalyst system (amine and peroxide) react with each other and initiate polymerization and hardening of the composition. A heat activating or self curing system enabled the curing of a big block of material of the invention, which can be subsequently machined (CAD/CAM) to dental devices with desired shapes.

In addition to the photoactive, chemical-activated, and heat activated agents, the composition high strength polymerizable dental materials of the invention may also include pigments, various stabilizers, plasticizers and fibers. Stabilizers can be used, for example, butylated hydroxytoluene (BHT); hydroquinone; hydroquinone monomethyl ether; benzoquinone; chloranil; phenol; butyl hydroxyanaline (BHT); tertiary butyl hydroquinone (TBHQ); tocopherol (Vitamin E); and the like. Preferably, butylated hydroxytoluene (BHT) and the methyl ether of hydroquinone (MEHQ) are used as the stabilizers (polymerization inhibitors). Other stabilizers, such UV absorbers, may also be used.

Fillers

The material herein may include an optional filler component that includes at least one filler. In one embodiment, the filler will typically be present in a range of about 5% to about 95% wt of the overall polymerizable composition. Preferably, the filler may be present in a range of about 30% to about 90%, and more preferably from about 50% to about 85% wt of the overall polymerizable composition. In another embodiment, the filler component may include a composite filler. The composite filler will typically be present in a range from about 0.0% to about 50% wt the overall polymerizable composition. Preferably, the composite filler may be present in a range from about 0.0% to about 20%, and more preferably from about 2% to about 10% wt the overall polymerizable composition.

It is appreciated that the filler may be provided as particles having a range of average particles sizes from about 0.01 micrometers to about 500 micrometers. The filler particles typically include organic particles, composite particles, inorganic particles or any combination thereof. The filler particles typically reduce polymerization shrinkage, improve wear resistance and/or modify the handling, mechanical and physical properties. Preferred inorganic fillers may include, but are not limited to, glasses formed from or including, barium, calcium, strontium, lanthanum, tantalum, and/or tungsten silicates and aluminates and/or aluminosilicates, silica, quartz, ceramics, nanoparticles (including metals, metal oxides, zirconia, yttria stabilized zirconia, zirconia alumina, alumina titania, etc.). In one embodiment, the inorganic filler particles may range in average particle sizes of from about 0.005 micrometers to about 20 micrometers. In another embodiment, composite fillers may be provided, which include cured composites formed from organic resin matrices and/or inorganic fillers as mentioned above. Preferably, organic resin matrices may be those utilized in this invention. Generally, composite fillers may have the same compositions as the final composites so as to have similar refractive index (RI) for desirable transparency. In another embodiment, the composite filler particles may be provided having a range of average particle sizes from about 0.1 micrometers to about 500 micrometers. Preferred organic fillers may be formed from cured resin matrices used in this invention and/or those polymers dispersible or compatible in resin matrices. Preferred organic fillers may have the similar compositions as those resin matrices used in final composites, easily dispersible in resin matrices, compositions with similar refractive indexes so as to obtain desirable transparency, or any combinations thereof. In yet another embodiment, the organic filler may be provided having a range of average particle sizes from about 0.1 micrometers to about 500 micrometers. Organic fillers, such as PMMA (polymethyl methacrylate), may also be used in small amount to simply improve the handling properties of formed composites.

The polymerizable dental materials of the invention are quickly and easily used and reshaped. The polymerizable dental materials may be worked and shaped for example by flowing, packing, molding, pressing, injecting, and/or carving. The worked polymerizable dental material is cured to give a surprising high strength and durable restoration. The polymerized dental composite of this invention offered higher flexural strength than those of commercially available dental composites.

Polymerizable dental materials of the invention offers cured resins and composites with surprising high strength. A preferred embodiment of the invention provides a high strength dental polymeric material (resin or composite) formed by light curing polymerizable dental material. In one embodiment, the high strength polymerizable material may be generally free of a filler component (e.g., less than about 5% wt filler, and preferably 0.0% wt filler) thereby providing a high strength polymeric matrix (resin) such as a high strength dental polymeric matrix (resin) as further discussed below. Preferably the high strength dental polymeric matrix (resin) may include a flexural modulus of at least about 400,000 psi and a flexural strength of at least about 20,000 psi. More preferably, the high strength dental polymeric matrix (resin) may include a flexural modulus of at least about 450,000 psi and a flexural strength of at least about 24,000 psi. Most preferably, the high strength dental polymeric matrix (resin) may include a flexural modulus of at least about 500,000 psi and a flexural strength of at least about 25,000 psi.

In a preferred embodiment, the high strength polymerizable material may include a filler component (e.g., greater than 5% wt filler) thereby providing a high strength polymeric matrix (composite) such as a high strength dental polymeric matrix (composite). Preferably, the high strength dental polymeric composite may include a flexural modulus of at least about 800,000 psi and a flexural strength of at least about 22,000 psi. More preferably, the high strength dental polymeric composite may include a flexural modulus of at least about 1,000,000 psi and a flexural strength of at least about 26,000 psi. Most preferably, high strength dental polymeric composite has a flexural modulus of at least about 1,200,000 psi and a flexural strength of at least about 28,000 psi. "Flexural strength and flexural modulus" as used herein refers to results of testing according to ASTM D790 (1997).

In order of increasing preference polymerization shrinkage of polymerizable dental resin (matrix) composition of the invention may be less than about 10% by volume, less than about 8% by volume, less than about 5% by volume. In order of increasing preference, polymerization shrinkage of polymerizable dental composite of the present invention may be less than about 5% by volume, less than 4 percent by volume, less than about 3% by volume, less than about 2% by volume. "High strength dental polymeric material" as used herein refers to material having a polymeric matrix (resin) having a flexural modulus of at least 400,000 psi and a flexural strength of at least 20,000 psi. High strength dental polymeric material (resin or composite) may be preferably formed into dental products including tooth restorative fillings, adhesives, sealants, for repair of defects in natural dentition, veneers, crowns, bridges, custom trays, artificial teeth, repairs for natural teeth, full dentures and partial dentures, by polymerization of polymerizable dental material.

Indirect Dental Laboratory Method

In one method for making the dental crown, which can be referred to as an indirect dental laboratory method, the dentist first takes an initial impression of the patient's entire dental anatomy including the tooth that will receive the crown using conventional impression-forming techniques. A negative impression of the teeth, including the unprepared tooth that will receive the crown, and surrounding gum tissue is formed. The dentist will then prepare the tooth that will receive the crown by performing "crown prep" work on the tooth by filing and grinding it to a "core" or "stump." The dentist then takes an impression of the prepared tooth.

The hardened impressions are sent to a dental laboratory that will fabricate the crown. The dental technician, at the laboratory, prepares a cast (or model) by pouring dental plaster or stone into the first hardened impression. This results in a finished plaster model having a shaped surface closely matching the patient's complete dental anatomy. Next, the laboratory technician fabricates a working model.

Once the model has been adequately reduced and prepared, a thin coating of a separating agent (for example, oxygen barrier coating available from Dentsply) is applied to the surface of the model. The technician first blocks out undercut with material, such as wax. Then separator is applied on the surface of prepped working model to make it easy to release from the model. If the dentist has prepared the tooth for receiving the crown in the office visit and taken an impression of the prepared tooth, a second dental model of the patient's dental anatomy including the crown-prepped tooth is fabricated. The dental laboratory may make this model, or the dentist may make this model at his/her office and send it to the laboratory. In such cases, the oxygen barrier coating or other separating agent is applied to the surface of this model.

Now, the crown is ready to be fabricated using the composite material of this invention. The shade of the composite material is carefully selected so that it matches the color of the patient's natural teeth. Next, the dental practitioner or laboratory technician places and molds layers of the dental composite material of this invention onto the surface to desired contour and tack cured for a few seconds, or 15 seconds in VLC light unit, such as an Enterra™ VLC curing unit. It may also be cured for 2 minutes in VLC light unit, such as an Enterra™ VLC curing unit (opaque resin may be used, where opaque layer may be built and cured as needed). Additional dental composite and enamel composite are placed, contoured and molded to form a crown on the targeted area of the dental model to form desired anatomy and occlusal contact. Then, a thin layer of a visible light curing (VLC) sealer or air barrier coating may be applied to the surface of the crown. Now, the model, which is seated with the composite material in a crown shape, is placed in a light-curing oven and irradiated with curing light and heated in accordance with a pre-determined curing cycle. The curing time will depend upon many different factors including the light-curing oven used. In general, the materials of this invention completely set and harden in the range of about one (1) to about fifteen (15) minutes.

If necessary, additional composite material can be added to touch-up the crown as it is seated on the model. Any excess composite material on the model should be removed.

After the cured dental crown and supporting model are removed from the oven, the assembly is cooled. Then, the crown is removed from the model using fingers, a crown remover, or other suitable instrument. The crown is finished and polished using conventional techniques. Aluminum oxide can be used to steam clean the interior surface of crown for subsequent effective bonding to reline or cement material at dentist's office. If needed, the crown also can be mechanically polished using buffing wheels and abrasives. Lastly, if the practitioner or technician wishes, a VLC sealant which provides a stain-resistant and glossy surface finish may be applied to the surface of the crown and the crown may be cured again in a light-curing oven.

The dental laboratory sends the finished crown back to the dentist. Once the dentist receives the crown, he or she can prepare the tooth that will receive the crown, if this has not already been done, by filing the tooth structure to a core or stump as described above. Then, the finished crown is affixed to the prepared tooth in the mouth of the patient using a suitable reline material, adhesive, dental cement or their combination. Conventional dental cements, as are known in the dental field, may be used in this step. In cases where a temporary crown has been mounted over the tooth structure, it is first removed and then the crown of this invention is affixed to the tooth using dental cement.

Other Methods

A preferred embodiment of the invention provides a prepared cavity in a tooth in a patient's mouth, which is then filled by injection from a syringe of dental filling material in accordance with the invention. Preferable, the flowable dental filling material contains at least 50 percent by weight filler and a polymerizable dental material selected from the group consisting of polymerizable dental resins, which includes high strength methacrylate or acrylate monomers of this invention. Thus, a syringe is provided having an inner chamber and a nozzle. The nozzle has a nozzle passage in fluid flow communication with the inner chamber. The inner chamber encloses polymerizable dental material of this invention. Then the polymerizable dental material is light cured to form a high strength dental polymeric material.

A preferred embodiment of the invention provides a prepared cavity in a tooth in a patient's mouth, which is then filled by injection from a dual barrel syringe of dental filling material in accordance with the invention. A self-curing composition is prepared from two components separately stored in a dual barrel. One component used to make the composition is a base paste and the other component is a catalyst paste. The base paste typically contains polymerizable resins such as high strength methacrylate or acrylate monomers of this invention and other commercially available monomers and oligomers; a free-radical polymerization accelerator such as a tertiary amine; and fillers such as silica, glasses, or alumina. Meanwhile, the catalyst paste typically includes polymerizable resins (preferable containing at least one of high strength methacrylate or acrylate monomers of this invention), free-radical polymerization initiator such as dibenzoyl peroxide, and fillers. To prepare the composition, the amine-containing base and peroxide-containing catalyst pastes are combined and mixed together upon injection. As the pastes are mixed together, the catalyst system (amine and peroxide) react with each other and initiate polymerization and hardening of the composition to form a high strength dental polymeric material. The polymerization process involves a reaction between the reducing agent (amine) and oxidizing agent (peroxide). This mechanism is commonly referred to as a redox mechanism.

Another preferred embodiment of the invention provides a prepared cavity in a tooth in a patient's mouth, which is then filled or packed by positioning in the prepared cavity a composition including at least 0 percent by volume filler and a polymerizable dental material selected from the group consisting of polymerizable dental resins, which includes at least one of high strength methacrylate or acrylate monomers of this invention. Then the polymerizable dental material is light cured to form high strength dental polymeric material with shrinkage during polymerization of less than 5 percent by volume. In the following examples, unless otherwise indicated, all parts and percentages are by weight; Lucirin TPO refers to 2,4,6-trimethylbenzoyldiphenylphosphine oxide made by BASF. LumiLux Blue LZ fluorescent agent is sold by Hoechst Celanese Corporation, a chemical family of dihydroxy terepthalate acid ester. Resins, SR348 (Ethoxylated$_2$ bisphenol A dimethacrylate) and SR368 [Tris (2-hydroxy ethyl) isocyanurate triacrylate] were purchased from SARTOMER Company, Inc. (Exton, Pa.).

The objective of this invention is to prepare resins, such as urethane, urea or urethane/urea monomers and oligomers having high flexural strengths, which can be formed into various high strength compositions and high strength composites for various dental applications. The urethanes resins are typically prepared from the reaction of hydroxyl end-capped (meth)acrylate or diol with (di)isocyanate-end capped monomer. The urea functional groups were introduced by using small amount of (di)amine based monomers or (meth)acrylates. The catalysts may be those known in the art to accelerate the reaction of the hydroxyl end-capped monomer with isocyanate-end capped monomer to form ethylenically unsaturated monomer or oligomer, for examples, tertiary amines and metal salts, e.g. stannous octoate and in particular dibutyl tin dilaurate.

Another objective of this invention is to provide light curable, heat curable or self curable compositions and composites with high flexural strength and low polymerization shrinkage for laboratory and chairside fabrication of esthetic dental restorations, such as dental crowns, bridges, inlays, onlays, veneers, implants, and other dental restorations.

Example 1

Preparation of Urethane Monomer (UCDPHMA)

A 500 mL flask was charged with 97.0 grams (0.499 mol) of 1,3-bis(isocyanatomethyl)cyclohexane under dry nitrogen flow and heated to about 60° C. under positive nitrogen pressure. To this reaction mixture, 6 drops of catalyst dibutyltin dilaurate were added. A mixture of 66.2 grams (0.509 mol) of 2-hydroxyethyl methacrylate, 72.9 grams (0.505 mol) of hydroxypropyl methacrylate and 0.36 grams of butylated hydroxytoluene (BHT) as an inhibitor were added over a period of one hour while the reaction temperature was maintained between 60° C. and 80° C. After about six hours stirring, the heat was turned off, and monomer was collected from the flask as viscous liquid and stored in a dry atmosphere.

Example 2

Preparation of Urethane Monomer (UCDPMAA)

A 500 mL flask was charged with 38.8 grams (0.200 mol) of 1,3-bis(isocyanatomethyl)cyclohexane under dry nitrogen flow and heated to about 60° C. under positive nitrogen pressure. To this reaction mixture, 3 drops of catalyst dibutyltin dilaurate were added. A mixture of 22.7 grams of 2-hydroxy-3-phenoxy propyl acrylate, 26.6 grams (0.204 mol) of 2-hydroxyethyl methacrylate, 11.5 grams (0.099 mol) of 2-hydroxyethyl acrylate and 0.10 grams of BHT as an inhibitor were added over a period of 70 minutes while the reaction temperature was maintained between 56° C. and 78° C. After about four hours stirring, the heat was turned off, and monomer was collected from the flask as viscous liquid and stored in a dry atmosphere.

Example 3

Preparation of Urethane Monomer (UCDPPA)

A 500 mL flask was charged with 38.8 grams (0.200 mol) of 1,3-bis(isocyanatomethyl)cyclohexane under dry nitrogen flow and heated to about 60° C. under positive nitrogen pressure. To this reaction mixture, 3 drops of catalyst dibutyltin dilaurate were added. A mixture of 29.2 grams (0.203 mol) of 2-hydroxypropyl methacrylate, 22.2 grams (0.100 mol) of 2-hydroxy-3-phenoxypropyl acrylate, 11.9 grams (0.102 mol) of 2-hydroxyethyl acrylate and 0.16 grams of BHT was added over a period of 50 minutes while the reaction temperature was maintained between 66° C. and 76° C. After about 4 hours and 25 minutes stirring under 78° C., the heat was turned off, and monomer was collected from the flask as viscous liquid and stored in a dry atmosphere.

Example 4

Preparation of Urethane Resin

A 250 mL flask was charged with 19.4 grams (0.10 mol) of 1,3-bis(isocyanatomethyl)cyclohexane under dry nitrogen flow and heated to about 48° C. under positive nitrogen pressure. To this reaction mixture, 2 drops of catalyst dibutyltin dilaurate were added. A mixture of 10.5 grams (0.047 mol) of 2-hydroxy-3-phenoxypropyl acrylate and 18.6 grams (0.143 mol) of 2-hydroxyethyl methacrylate containing 0.055 grams of BHT as an inhibitor was prepared and added over a period of one hour and 25 minutes while the reaction temperature was maintained between 65° C. and 75° C. After the addition of 90% above mixture, 1.9 gram (0.013 mol) of UNOXOL™ Diol (from Dow Chemical Company, Midland, Mich.) was added before the final addition of remaining 10% above mixture. UNOXOL™ Diol is a cycloaliphatic diol that is composed of approximately a 1:1 ratio of (cis, trans-1,3-cyclohexanedimethanol and (cis, trans)-1,4-cyclohexanedimethanol. After about another 5 hours stirring, the heat was turned off, and monomer was collected from the flask as viscous colorless liquid and stored in a dry atmosphere.

Example 5

Preparation of Urethane Monomer (UCDPMA)

A 250 mL flask was charged with 19.4 grams (0.100 mol) of 1,3-bis(isocyanatomethyl)cyclohexane under dry nitrogen flow and heated to about 60° C. under positive nitrogen pressure. To this reaction mixture, 2 drops of catalyst dibutyltin dilaurate were added. A mixture of 21.9 grams (0.168 mol) of 2-hydroxyethyl methacrylate, 7.5 grams (0.034 mol) of 2-hydroxy-3-phenoxypropyl acrylate and 0.05 grams of BHT was added over a period of 30 minutes while the reaction temperature was maintained between 62° C. and 76° C. After about 4 hours and 35 minutes stirring under 78° C., the heat was turned off, and monomer was collected from the flask as viscous liquid and stored in a dry atmosphere.

Example 6

Preparation of Urethane/Urea Resin

A 250 mL flask was charged with 19.4 grams (0.10 mol) of 1,3-bis(isocyanatomethyl)cyclohexane under dry nitrogen flow and heated to about 64° C. under positive nitrogen pressure. To this reaction mixture, 2 drops of catalyst dibutyltin dilaurate were added. A mixture of 10.5 grams (0.047 mol) of 2-hydroxy-3-phenoxypropyl acrylate and 16.15 grams (0.139 mol) of 2-hydroxyethyl acrylate containing 0.05 grams of BHT as an inhibitor was prepared and added over a period of one hour and 25 minutes while the reaction temperature was maintained between 64° C. and 75° C. After the addition of 90% above mixture, 1.6 gram (0.014 mol) of 1,2-diaminocyclohexane was added before the final addition of remaining 10% above mixture. After about another 5 hours stirring, the heat was turned off, and monomer was collected from the flask as viscous yellow tint liquid and stored in a dry atmosphere.

Examples 7A Through 7D

Tables 1 and 2 show the components of the compositions of Examples 7A through 7D. The compositions of Examples 7A through 7D were prepared by mixing the components shown in Tables 1 and 2 at 85° C. The composites of this invention as well as other commercially available composites can be used as composite fillers. It is preferable that the composite and composite filler have the same composition. Composite filler was prepared by grinding a light cured composite with a diamond bur. Here a light cured composite (Example 7A) used has a composition of 69.00 weight percent of silanated barium aluminoflurosilicate glass (BAFG) particles having an average particle size of from about 0.1 to about 1 micrometers, 19.00 weight percent of UCDPMAA, 6.65 weight percent of SR368, 5.00 weight percent of TEGDMA (triethyleneglycol dimethacrylate), 0.25 weight percent of ALF and 0.10 weight percent of Lucirin TPO. ALF is referred to a light initiating material comprising camphorquinone (CQ); butylated hydroxytoluene (BHT); N,N-dimethylaminoneopentyl acrylate, γ-methacryloxypropylsilane and methacrylic acid.

TABLE 1

| COMPONENTS | Example 7A (wt %) | Example 7B (wt %) |
|---|---|---|
| UCDPMAA (Example 2) | 19.00 | |
| UCDPHMA (Example 1) | | 30.60 |
| SR368 | 6.65 | |
| TEGDMA | 5.00 | |
| 2,4,6-trimethylbenzoyldiphenyl phosphine oxide (Lucirin TPO) | 0.10 | 0.10 |
| Camphorquinone | 0.033 | 0.040 |
| N,N-dimethyl-aminoneopentyl acrylate | 0.115 | 0.138 |
| Methacrylic Acid | 0.057 | 0.069 |
| Butylated Hydroxytoluene | 0.004 | 0.004 |
| γ-methacryloxypropylsilane | 0.041 | 0.049 |

TABLE 1-continued

| COMPONENTS | Example 7A (wt %) | Example 7B (wt %) |
|---|---|---|
| Silanated barium aluminoflurosilicate glass (BAFG) * | | 13.00 |
| Silanated barium aluminoflurosilicate glass (BAFG) ** | 69.00 | 56.00 |

\* Particles having an average particle size of about 1 to about 10 micrometers.
\*\* Particles having an average particle size of about 0.1 to about 1 micrometers.

TABLE 2

| COMPONENTS | Example 7C (wt %) | Example 7D (wt %) |
|---|---|---|
| UCDPMAA (Example 2) | 16.40 | 14.96 |
| SR368 | 5.67 | 5.17 |
| TEGDMA | 4.20 | 3.83 |
| 2,4,6-trimethylbenzoyl-diphenylphosphine oxide (Lucirin TPO) | 0.067 | 0.060 |
| Camphorquinone | 0.044 | 0.040 |
| N,N-dimethyl-aminoneopentyl acrylate | 0.153 | 0.138 |
| Methacrylic Acid | 0.076 | 0.069 |
| Butylated Hydroxytoluene | 0.005 | 0.004 |
| γ-methacryloxypropylsilane | 0.055 | 0.049 |
| silanated barium aluminoflurosilicate glass (BAFG)[1] | | 16.22 |
| silanated barium aluminoflurosilicate glass (BAFG)[2] | 23.33 | 10.82 |
| silanated barium aluminoflurosilicate glass (BAFG)[3] | 50.00 | 24.32 |
| silanated barium aluminoflurosilicate glass (BAFG)[4] | | 24.32 |

[1]Particles having an average particle size of about 1 to about 10 micrometers.
[2]Particles having an average particle size of about 0.5 to about 5 micrometers.
[3]Particles having an average particle size of about 0.2 to about 2 micrometers.
[4]Particles having an average particle size of about 0.1 to about 1 micrometers.

Table 3 shows the physical properties of above composite formulations. Table 4 gives the physical properties of the commercially available indirect crown and bridge and restorative products, which have been polymerized according to manufacturing instructions. Table 3 showed the composites of this invention have superior flexural strength and modulus compared to commercially available materials shown in Table 4.

TABLE 3

| Property/Characteristic | Example 7A | Example 7B | Example 7C | Example 7D |
|---|---|---|---|---|
| Localized Wear (at 37° C.) - mm$^3$ (samples were cured for 10 minutes in the Enterra light curing unit | 0.028 | 0.0089 | | |
| Flexural Strength - psi | 30,800 | 30,600 (post cure) | 31,800 | 30,200 |
| Flexural Modulus - kpsi | 1,600 | 1,890 | 2,040 | 2,270 |

TABLE 4

Comparative Examples

| Property/Characteristic | Example 7E (Radica) | Example 7F (Gradia) | Example 7G (Sinfony) | Example 7H (TPH3) from Caulk |
|---|---|---|---|---|
| Localized Wear (at 23° C.) - mm$^3$ (samples were cured for 10 minutes in the Enterra light curing unit | 0.029 | 0.047 | 0.049 | 0.014 |
| Flexural Strength - psi | 22,900 | 14,600 | 15,800 | 19,300 |
| Flexural Modulus - kpsi | 1,440 | 890 | 660 | 1,300 |
| Compressive Strength - MPa | 350 | | | 310 |

Compressive Strength of the polymerized composite compositions of Examples 7A through 7D, 7E and 7H was measured using 50 kN load cell set to run at 2,000 pounds with crosshead speed at 2 inches (50.8 mm)/per minute. Compressive strength testing specimens were prepared by following the procedure of U.S. Pat. No. 6,387,981. Each composite was packed into a 4 mm inside diameter glass tube, capped with silicone rubber plugs and axially compressed at about 0.28 MPa for 15 minutes, then light cured for 10 minutes in Eclipse light curing unit (voltage at 37.5 V, blowers at 80 percent). Cured samples were cut on a diamond saw to form cylindrical plugs 8 mm long and stored in distilled water at 37° C. for 24 hours and then measured for compressive strength.

Volume loss (cubic mm at 400,000 cycles), was used as a measure of the wear resistance of the polymerized composite compositions of Examples 7A through 7H. A three body cyclic abrasion wear machine (Leinfelder method/University of Alabama in vitro) was used to determine volume loss.

Flexural Strength and Flexural Modulus of the polymerized composite compositions of Examples 7A to 7H were measured by using three-point bend test on Instron bending unit according to ISO10477. Samples from 7A to 7D were cured in metal molds in an Enterra light curing unit for 10 minutes (5 minutes cure on top surface followed by 5 minutes cure on opposite side). Others were cured according to manufacturing instructions.

Examples 8A

Table 5 shows the components of the compositions of Examples 8A. The composition of Examples 8A was prepared by mixing the components shown in Table 5 under 85° C. in 50 minutes. This composite was transferred into a preheated mold at 90° C. and heat cured under pressure for 4 hours with gradually increased temperature to 150° C. from one heating plate first and finally cured with both heating plates. Some of the samples were subsequently post heat treated for 2 hours at 120° C. as indicated.

TABLE 5

| COMPONENTS | Example 8A (grams) |
|---|---|
| UCDPHMA (Example 1) | 25.1 |
| TBDMA[a] | 3.446 |
| t-butyl peroxy benzoate | 0.4 |
| Titanium dioxide | 0.050 |
| Yellow Iron oxide | 0.0048 |
| Red-Brown Pigment | 0.0002 |
| Black Pigment | |
| LumiLux Blue LZ fluorescent agent | 0.001 |
| silanated barium aluminoflurosilicate glass (BAFG) [b] | 13 |
| silanated barium aluminoflurosilicate glass (BAFG) [c] | 58 |

[a] TBDMA is an oligomer prepared according to Example 1 of U.S. Pat. No. 6,592,369
[b] Particles having an average particle size of about 1 to about 10 micrometers.
[c] Particles having an average particle size of about 0.1 to about 1 micrometers.

Table 6 shows the physical properties of the products of Examples 8A, which were polymerized by heat curing. They are tested the same way as those in Example 7A through 7D.

TABLE 6

| Property/Characteristic | Example 8A |
|---|---|
| Localized Wear (at 37° C.) - mm³ (4 hours heat cured) | 0.0181 |
| Localized Wear (at 37° C.) - mm³ (samples were heat cured with post treatment) | 0.0108 |
| Flexural Strength - psi (4 hours heat cured) | 29,700 |
| Flexural Modulus - kpsi (4 hours heat cured) | 1,690 |
| Flexural Strength - psi (samples were heat cured with post treatment) | 29,200 |
| Flexural Modulus - kpsi (samples were heat cured with post treatment) | 1,680 |
| Compressive Strength - MPa (samples were heat cured with post treatment) | 430 |

Examples 8B and 8C

Table 7 shows the components of the compositions of Examples 8B. The compositions of Examples 8B and 8C were prepared by mixing and degassing the components shown in Tables 7 at 85° C.

TABLE 7

| COMPONENTS | Example 8B (grams) | Example 8C (grams) |
|---|---|---|
| UCDPMAA (Example 2) | 15.44 | 15.525 |
| SR368 | 5.325 | 5.325 |
| TEGDMA | 3.9525 | 3.955 |
| Titanium dioxide | 0.0502 | 0.019 |
| Yellow Iron oxide | 0.0065 | |
| Red-Brown Pigment | 0.0001 | |
| Black Pigment | 0.0004 | |
| 2,4,6-trimethylbenzoyldiphenyl phosphine oxide (Lucirin TPO) | 0.045 | 0.0325 |
| Camphorquinone | 0.0316 | 0.0216 |
| N,N-dimethyl-aminoneopentyl acrylate | 0.1094 | 0.0749 |
| Methacrylic Acid | 0.0546 | 0.0374 |

TABLE 7-continued

| COMPONENTS | Example 8B (grams) | Example 8C (grams) |
|---|---|---|
| Butylated Hydroxytoluene | 0.0031 | 0.0021 |
| γ-methacryloxypropylsilane | 0.0388 | 0.0265 |
| silanated barium aluminoflurosilicate glass (BAFG) * | 74.9428 | 74.981 |

* Particles having an average particle size of about 0.5 to about 2 micrometers.

Table 8 shows the physical properties of the products of Examples 8B and 8C, which were polymerized by light curing. They are tested the same way as those in Example 7A through 7D. The water solubility and water sorption were tested according to ISO 10477 and samples were cured by 30 seconds tack cure on top surface and followed by 5 minutes final cure on opposite side.

TABLE 8

| Property/Characteristic | Example 8B | Example 8C |
|---|---|---|
| Localized Wear (at 37° C.) - mm³ (samples were cured for 30 seconds + 5 minutes in the Enterra light curing unit) | 0.0298 | 0.0205 |
| Flexural Strength - psi | 31,200 | 33,000 |
| Flexural Modulus - kpsi | 1,780 | 1,870 |
| Compressive Strength - MPa | 516 | 508 |
| Water Sorption (μg/mm³) | 18.7 | 18.8 |
| Water Solubility (μg/mm³) | 0 | 0.4 |

Examples 9A Through 9C

As mentioned above, the high strength polymerizable material may be generally free of a filler component (e.g., less than about 5% wt filler, and preferably 0.0% wt filler) thereby providing a high strength polymeric matrix (resin) such as a high strength dental polymeric matrix (resin).

When provided, the high strength polymeric matrix (resin) being generally free of a filler component may comprise a first polymerizable component that includes at least one polymerizable acrylic compound. The polymerizable acrylic compound (e.g., first polymerizable component) will typically be present in an amount of at least 50% wt, and more preferably at least about 75% wt the overall polymerizable matrix composition. The overall polymerizable matrix composition also typically includes less than about 100% wt and more typically less than about 99% wt of the polymerizable acrylic compound. For example, the polymerizable acrylic compound will typically be present in a range of about 50% to about 100%, and more typically from about 75% to about 99% wt of the overall polymerizable matrix composition.

The high strength polymeric matrix (resin) being generally free of a filler component may comprise at least one initiating component (e.g., system) to effectuate curing of the material. The initiating component will typically be present in an amount of at least 0.01% wt, and more preferably at least about 0.05% wt the overall polymerizable matrix composition. The overall polymerizable matrix composition also typically includes less than about 10% wt and more typically less than about 5% wt of the initiating component. For example, the initiating component will typically be present in a range of about 0.01% to about 10%, and more typically from about 0.05% to about 5% wt of the overall polymerizable matrix composition. Furthermore, the "ALF" initiating system may be present in an amount ranging from about 0.25% wt to about 5% wt, and preferably from about 0.5% wt to about 3% wt of the overall polymerizable composition. It is appreciated that in one embodiment, the material may include an initiating system comprising both the "ALF" initiating system and Lucirin-TPO for curing the composition.

In addition to the photoactive, chemical-activated, and heat activated agents, the high strength polymeric matrix (resin) of the invention may also include pigments, various stabilizers, plasticizers. Stabilizers can be used, for example, butylated hydroxytoluene (BHT); hydroquinone; hydroquinone monomethyl ether; benzoquinone; chloranil; phenol; butyl hydroxyanaline (BHT); tertiary butyl hydroquinone (TBHQ); tocopherol (Vitamin E); and the like. Preferably, butylated hydroxytoluene (BHT) and the methyl ether of hydroquinone (MEHQ) are used as the stabilizers (polymerization inhibitors). Other stabilizers, such as UV absorbers, may also be used.

Table 9 shows the components of the high strength polymeric matrix (resin) compositions of Examples 9A through 9C, which were prepared free of inorganic fillers. It was appreciated that the high strength polymeric matrix (resin) compositions provided surprising high strength as compared to commercially available dental resin compositions as shown in Table 10.

TABLE 9

| COMPONENTS | Example 9A (grams) | Example 9B (grams) | Example 9C (grams) |
|---|---|---|---|
| UCDPMAA (Example 2) | 98.7 | | |
| Urethane Resin (Example 4) | | 98.7 | |
| UCDPMA (Example 5) | | | 98.7 |
| 2,4,6-trimethylbenzoyl-diphenylphosphine oxide (Lucirin TPO) | 0.3 | 0.3 | 0.3 |
| Camphorquinone | 0.1331 | 0.1331 | 0.1331 |
| N,N-dimethyl-aminoneopentyl acrylate | 0.4605 | 0.4605 | 0.4605 |
| Methacrylic Acid | 0.2302 | 0.2302 | 0.2302 |
| Butylated Hydroxytoluene | 0.0131 | 0.0131 | 0.0131 |
| γ-methacryloxy-propylsilane | 0.1631 | 0.1631 | 0.1631 |

The compositions of Examples 9A through 9C were prepared by mixing the components shown in Table 9 at 90° C.

TABLE 10

Comparative Commercial Examples

| COMPONENTS | Example 9D (grams) | Example 9E (grams) | Example 9F (grams) |
|---|---|---|---|
| TBDMA* | 98.7 | | |
| SR348 | | 98.7 | |
| UDMA (7,7,9-trimethyl-4,13-dioxo-5,12-diazahexadecane-1,16-diol dimethacrylate) | | | 98.7 |
| 2,4,6-trimethylbenzoyl-diphenylphosphine oxide (Lucirin TPO) | 0.3 | 0.3 | 0.3 |
| Camphorquinone | 0.1331 | 0.1331 | 0.1331 |
| N,N-dimethyl-aminoneopentyl acrylate | 0.4605 | 0.4605 | 0.4605 |
| Methacrylic Acid | 0.2302 | 0.2302 | 0.2302 |
| Butylated Hydroxytoluene | 0.0131 | 0.0131 | 0.0131 |
| γ-methacryloxy-propylsilane | 0.1631 | 0.1631 | 0.1631 |

*TBDMA is an oligomer prepared according to Example 1 of U.S. Pat. No. 6,592,369

Table 11 shows the physical properties of the products formed from the high strength polymeric matrix (resin) compositions of Examples 9A-9C, (See Table 9), which have been polymerized by light curing. Flexural Strength and Flexural Modulus of the compositions of Examples 9A to 9F were measured by using three-point bend test on Instron bending unit according to ISO10477. Samples from 9A to 9F were cured in metal molds in an Enterra light curing unit for 10 minutes.

TABLE 11

| Property/Characteristic | Example 9A | Example 9B | Example 9C |
|---|---|---|---|
| Flexural Strength - psi | 25,500 | 25,100 | 26,500 |
| Flexural Modulus - kpsi | 535 | 554 | 565 |

Table 12 shows the physical properties of the comparative products of Examples 9D-9F (See Table 10, Comparative Commercial Examples), which have been polymerized by light curing.

TABLE 12

| Property/Characteristic | Example 9D | Example 9E | Example 9F |
|---|---|---|---|
| Flexural Strength - psi | 18,600 | 18,000 | 19,400 |
| Flexural Modulus - kpsi | 430 | 470 | 380 |

It is appreciated as shown in Table 11 that the new high strength polymeric matrix (resin) compositions of this invention have much higher flexural strength and/or modulus than typical dental resins (e.g., Table 12) used in current commercially available products.

Advantageously, this invention provides high strength materials for making long-term dental crowns, bridges, inlays, onlays, veneers, implants, and other dental restorations. In one version, a dental laboratory can make the restoration using the high strength material of this invention. This method involves dispensing and applying high strength polymerizable material over an area of a pre-formed dental model that will receive the restoration. The material may comprise polymerizable acrylic compound, polymerization system capable of being activated by light or heat for polymerizing the composition, and filler material. A substructure such as a metal coping, ceramic substructure, or fiber-reinforced polymeric substructure can be used to support the polymerizable material. The high strength material, which is preferably a composite material containing filler particulate, is applied and shaped to form a shape-stable uncured restoration on the dental model. Light is used to irradiate the composite material so that it cures and forms a hardened restoration directly on the model. Finally, the restoration is removed, finished, and polished. A visible light-curing sealant can be applied to provide a stain-resistant and glossy surface finish to the restoration if desired. The restoration is now ready to be mounted on a patient's tooth.

It should be understood that while the present invention has been described in considerable detail with respect to certain specific embodiments thereof, it should not be considered limited to such embodiments but may be used in other ways without departure from the spirit of the invention and the scope of the appended claims.

The invention claimed is:
1. A dental component comprising a composition, the composition comprising:
about 1 to about 99% wt of one or more urethane di or multi(meth)acrylate derivatives of 1,3-bis(isocyanatomethyl)cyclohexane characterized by one of the following formulas:

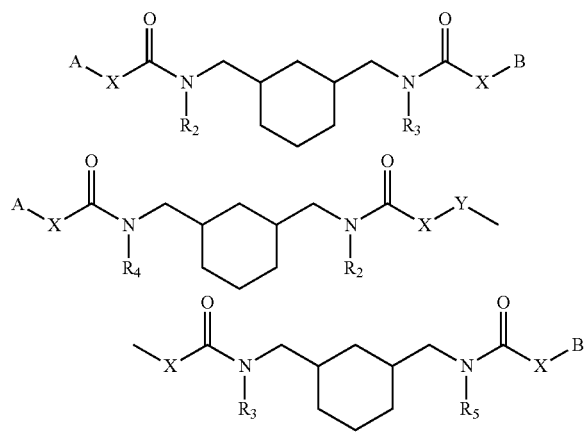

in which:
X is oxygen, nitrogen, or $NR_1$, where:
$R_1$ is hydrogen, a C1-C14 alkyl group, a C6-C14 cyclic group, C1-C14 cyclic alkyl group, a C6-C14 aromatic group, a C1-C14 aromatic alkyl group, or any combination thereof;
$R_2$, $R_3$, $R_4$ and $R_5$ is hydrogen, a C1-C14 alkyl group, a C6-C14 cyclic group, C1-C14 cyclic alkyl group, a C6-C14 aromatic group, a C1-C14 aromatic alkyl group, or any combination thereof;
Y is a C1-C14 alkyl group, a C6-C14 cyclic group, a C1-C14 cyclic alkyl group, a C6-C14 aromatic group, a C1-C14 aromatic alkyl group, or any combination thereof;
A and B independently of each other stand for one of the following formulas:

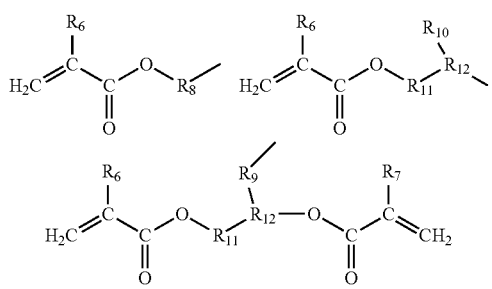

where:
$R_6$ and $R_7$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen or sulfur atoms;
$R_8$ and $R_9$ is a C1-C12 difunctional alkylene, a C1-C12 alkyl group, a C6-C12 cyclic group, a C1-C12 cyclic alkyl group, a C6-C12 aromatic group, a C1-C12 aromatic alkyl group, or any combination thereof, which can be interrupted by oxygen or sulfur atoms;
$R_{10}$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen or sulfur atoms;
$R_{11}$ represents a C1-C14 difunctional alkylene, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen or sulfur atoms; and
$R_{12}$ represents a C1-C8 trifunctional alkyl group, which can be interrupted by oxygen or sulfur atoms; and
about 0.001 to about 10% wt of a visible light and/or blue light initiator for the radical polymerization.

2. A dental component according to claim 1, wherein the composition further comprising about 5% to about 95% of at least one filler.

3. A dental component according to claim 2, wherein A and B are the same.

4. A dental component according to claim 1, wherein the composition includes about 10% to 50% wt of one or more of the urethane di or multi(meth)acrylate derivatives.

5. A dental component according to claim 4, wherein A and B are the same.

6. A dental component according to claim 5, wherein the composition is substantially free of a filler.

7. A dental component according to claim 4, wherein the composition is substantially free of a filler.

8. A dental component according to claim 1, wherein the composition includes about 15% to 40% wt of one or more of the urethane di or multi(meth)acrylate derivatives; about 30% to about 90% wt fillers; and 0.005% to about 5% of an initiator for the radical polymerization.

9. A dental component according to claim 8, wherein A and B are the same.

10. A dental component according to claim 9, wherein the composition is substantially free of a filler.

11. A dental component according to claim 1, wherein A and B are the same.

12. A dental component according to claim 1, wherein the composition is substantially free of a filler.

13. A dental component according to claim 1, wherein:
(i) the one or more urethane di or multi(meth)acrylate derivatives of 1,3-bis(isocyanatomethyl)cyclohexane is present in an amount of about 10 to about 50% wt; and
(ii) the composition further comprises about 30 to about 90% wt of at least one filler.

14. A dental component according to claim 13, wherein A and B are the same.

15. A dental component according to claim 1, wherein the dental component exhibits a flexural modulus of at least about 800,000 psi and a flexural strength is at least about 22,000 psi.

16. A dental component according to claim 1, wherein the dental component exhibits a flexural modulus of at least about 1,200,000 psi and a flexural strength is at least about 28,000 psi.

17. A dental component according to claim 1, wherein the dental component exhibits a flexural modulus of at least 400,000 psi and a flexural strength of at least 20,000 psi.

* * * * *